United States Patent [19]
Walseth et al.

[11] Patent Number: 5,486,604
[45] Date of Patent: Jan. 23, 1996

[54] CYCLIC ADP RIBOSE ANTAGONISTS

[75] Inventors: Timothy F. Walseth, Roseville; Hon-Cheung Lee, Woodbury; Robert A. Aarhus, Brooklyn Park, all of Minn.

[73] Assignee: Regents of the University of Minnesota, Minneapolis, Minn.

[21] Appl. No.: 148,646

[22] Filed: Nov. 1, 1993

[51] Int. Cl.$^6$ ............................ C07H 19/23; A61K 51/00
[52] U.S. Cl. .................. 536/26.13; 536/26.2; 536/26.21; 536/26.23; 536/26.24
[58] Field of Search ............................ 536/26.13, 26.24, 536/26.2, 26.21, 26.23; 424/1.1

[56] References Cited

U.S. PATENT DOCUMENTS 5,202,426  4/1993  Strumwasser et al. .................... 436/27

OTHER PUBLICATIONS

"Identification of Cyclic ADP–Ribose–Binding Proteins by Photoaffinity Labeling", Journal of Biological Chemistry, 1993.

"Calcium Mobilization by Dual Receptors During Fertilization of Sea Urchin Eggs", Science, 16 Jul. 1993, vol. 261, pp. 352–355.

"Specific Binding of Cyclic ADP–Ribose to Calcium–Storing Microsomes From Sea Urchin Eggs", Journal of Biological Chemistry, 1991, vol. 266, No. 4, 5 Feb., pp. 2276–2281.

"ADP–Ribosyl Cyclase: An Enzyme that Cyclized NAD+ Into a Calcium–Mobolizing Metabolite", The American Society for Cell Biology, 1991, Cell Regulation, vol. 2, 203–209.

"Synthesis and Characterization of Antagonists of Cyclic–ADP–Ribose–Induced Ca$^{2+}$ Release", 1993 Elsevier Science Publishers.

"Potentiation of Calcium–and Caffeine–Induced Calcium Release by Cyclic ADP–Ribose", The Journal of Biological Chemistry, 1993.

"Production and Hydrolysis of Cyclic ADP–Ribose at the Outer Surface of Human Erythrocytes", Biochemical and Biophysical Research Communications, vol. 191, No. 2, 1993.

"Wide Distribution of an Enzyme that Catalyzes the Hydrolysis of Cyclic ADP–Ribose", Biochimica et Biophysica Acts, 1993, Elsevier Science Publishers.

"Ca$^{2+}$–Induced Ca$^{2+}$ Release in Sea Urchin Egg Homogenates:Modulatoin by Cyclic ADP–Ribose", Science, vol. 253, 6 Sep. 1991.

"Determination of Endogenous Levels of Cyclic ADP–Ribose in Rat Tissues", Biochimica et Biophysica Acts, 1991 Elseview Science Publishers.

"Novel Mechanism of Intracellular Calcium Release in Pituitary Cells", The Journal of Biological Chemistry, vol. 166, No. 26, Issue of Sep. 15, pp. 16985–16988, 1991.

"Comparison of Ca$^{2+}$ Mobilizing Activities of Cyclic ADP–Ribose and Inositol Trisphosphate", 1990 by The American Society for Cell Biology, Cell Regulation, vol. 1, 279–290, Feb. 1990.

"Widespread Occurrence in Animal Tissues of an Enzyme Catalyzing the Conversion of NAD+ Into a Cyclic Metabolite With Intracellular Ca$^{2+}$–Mobilizing Activity", The Journal of Biological Chemistry, 1989, vol. 264, No. 20, Jul. Issue pp. 11725–11731.

"Structural Determination of a Cyclic Metabolite of NAD+ With Intracellular Ca$^{2+}$–Mobilizing Activity", The Journal of Biological Chyemistry 1989, vol. 264, No. 3, Jan. Issue, pp. 1608–1615.

"Pyridine Nucleotide Metabolites Stimulate Calcium Release From Sea Urchin Egg Microsomes Desensitized to Inositol Trisphosphate", The Journal of Biological Chemistry, 1987, vol. 262, No. 20 Jul. Issue pp. 9561–9568.

Primary Examiner—Douglas W. Robinson
Assistant Examiner—James O. Wilson
Attorney, Agent, or Firm—Vidas, Arrett & Steinkraus

[57] ABSTRACT

Cyclic ADP-ribose (cADPR) analogs block cADPR from releasing Ca$^{+2}$, and also inhibit cADPR from potentiating Ca$^{+2}$ release induced by either divalent cations or by caffeine. 8-amino-cADPR and two other 8-substituted analogs were also synthesized. Both 8-Br- and 8-azido-cADPR were also antagonists, although with less potency than 8-amino-cADPR. These results show that alterations at the 8-position of the adenine group do not inhibit cADPR from binding to its receptor but do eliminate the ability of the metabolite to activate the Ca$^{+2}$ release mechanism.

4 Claims, 11 Drawing Sheets

Figuree 2

5,486,604

CYCLIC ADP RIBOSE ANTAGONISTS

STATEMENT AS TO RIGHTS

This invention was made with government support under grant HD-17484 awarded by the National Institute of Health. The Government has certain rights in this invention.

BACKGROUND OF THE INVENTION

1. Field of the Invention

This invention relates to 8-substituted-cADPR (analogs of cADPR modified at the 8-position of the adenine ring). They are antagonists to $Ca^{+2}$ mobilizing activity.

2. Description of the Related Art

U.S. Pat. No. 5,202,426 to Strumwasser et al describes NAD cyclase useful in producing cADPR from NAD. The inventors postulate that analogs could be prepared to cADPR that would block the effect of cADPR on cADPR-receptors.

Calcium channels are regions of cell membranes which facilitate the transport and secretion of fluids and electrolytes, such as calcium, into the cell [Rasmussen, H. *N.E.J. Med.* 314:1094–1101 (1986)]. These channels can be blocked using a class of compounds known as calcium channel blockers or calcium entry blockers. Compounds included in this class are verapamil, cobalt chloride and other biologically acceptable salts of cobalt, and hydropyridine compounds, such as nifedipine.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R.§1.56(a) exists.

SUMMARY OF THE INVENTION

The invention provides cyclic ADP Ribose (cADPR) antagonists. Results show that alterations at the 8-position of the adenine group did not inhibit cADPR from binding to its receptor but did eliminate its ability to activate $Ca^{+2}$ release. Furthermore, 8-amino-cADPR, the most potent antagonist synthesized, was also able to block the potentiating effect of cADPR on $Ca^{+2}$ release induced by divalent cations and caffeine.

BRIEF DESCRIPTION OF THE DRAWINGS

A detailed description of the invention is hereafter described with specific reference being made to the drawings in which.

DESCRIPTION OF THE PREFERRED EMBODIMENTS

Figure 1:
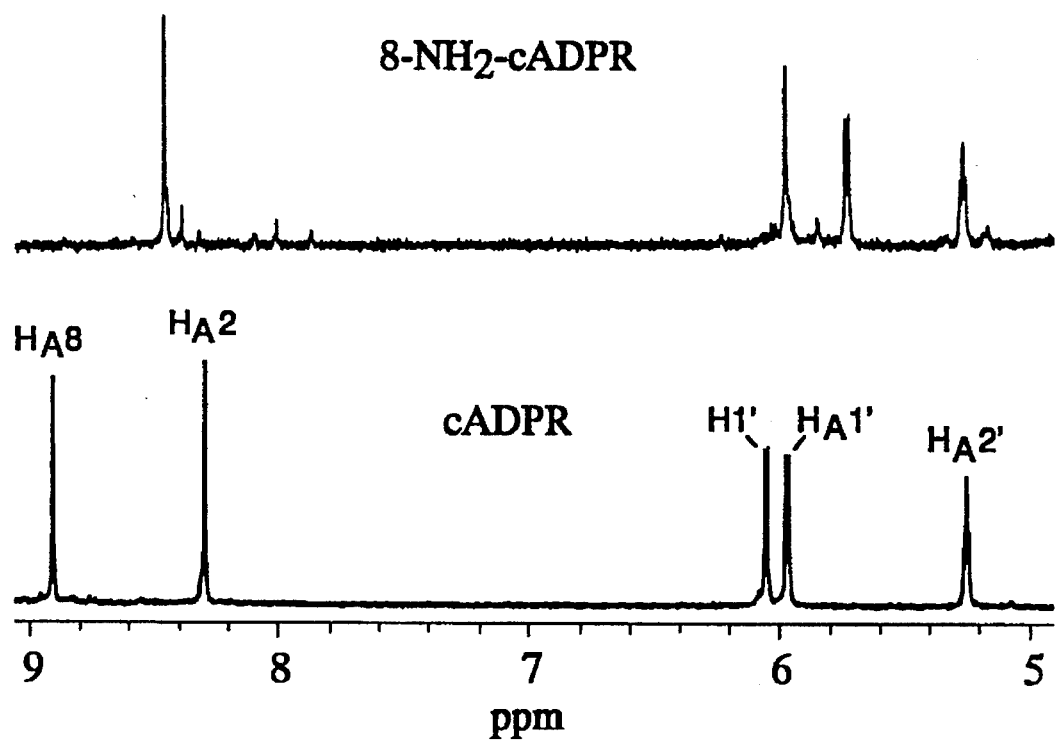
FIG. 1 Proton NMR spectra of 8-amino-cADPR and cADPR. Peaks labeled $H_A2$ and $H_A8$ correspond to the 2- and 8-proton on the adenine ring respectively, H1' correspond to the anomeric proton of the terminal ribose, $H_A1'$ and $H_A2'$ correspond to the 1- and 2-proton of the adeninyl ribose.

Cyclic ADP-ribose (cADPR) is a metabolite of $NAD^+$ that is as effective as inositol trisphosphate in mobilizing intracellular $Ca^{+2}$ stores in sea urchin eggs (Clapper, D. L., Walseth, T. F., Dargie, P. J. and Lee, H. C. (1987) *J. Biol. Chem.* 262, 9561–9568; Dargie, P. J., Agre, M. C., and Lee, Hon. C. (1990) *Cell Regulation* 1, 279–290.) and rat pituitary cells (Koshiyama, H., Lee, H. C. and Tashijan, A. H. Jr. (1991) *J. Biol. Chem.* 266, 16985–16988.). The metabolite itself (Walseth, T. F., Aarhus, R., Zeleznikar, R. J. Jr. and Lee, H. C. (1991) *Biochim. Biophys. Acta* 1094, 113–120) as well as its synthesizing enzyme, ADP ribosyl cyclase (Rusinko, N. and Lee, H. C. (1989) *J. Biol. Chem.* 264, 11725–11731; Lee, H. C. and Aarhus, R. (1991) *Cell Regulation* 2, 203–209) are present in various mammalian and invertebrate tissues. The cyclic structure of the metabolite is formed by linking the adenine group of $NAD^+$ to the terminal ribosyl unit and displacing the nicotinamide moiety (Lee, H. C., Walseth, T. F., Bratt, G. T., Hayes, R. N., and Clapper, D. L. (1989) *J. Biol. Chem.* 264, 1608–1615). The $Ca^{+2}$ release mechanism that is activated by cADPR is totally distinct from the inositol trisphosphate pathway. It is insensitive to blockage by heparin, a competitive inhibitor of the receptor for inositol trisphosphate. Furthermore, inositol trisphosphate was shown to complete at least a thousand times less effectively than cADPR for the specific microsomal binding site for cADPR (Lee, H. C. (1991) *J. Biol. Chem.* 266, 2276–2281).

Accumulating evidence (Galione, A., Lee, H. C. and Busa, W. B. (1991) *Science* 253, 1143–1146; Galione, A. (1992) *Trends Pharmacol. Sci.* 13, 304–306; Lee, H. C. (1993) *J. Biol. Chem.* 268, 293–299) suggests that the $Ca^{+2}$ release system activated by cADPR may be related to another major $Ca^{+2}$ mobilizing mechanism in cells, the $Ca^{+2}$ induced $Ca^{+2}$ release (CICR) system (Endo, M. (1977) *Physiol. Rev.* 57, 71–108; Fleischer, S. and Inui, M. (1989) *Annu. Rev. Biophys. Chem.* 18, 333–364). Both caffeine and ryanodine, pharmacological activators of CICR system in muscle, not only can induce maximal $Ca^{+2}$ release from the egg homogenates but also cause desensitization to cADPR. The reverse is also true since egg homogenates become insensitive to caffeine and ryanodine after prior treatment with saturating concentrations of cADPR. These results suggest that cADPR releases $Ca^{+2}$ from the same stores as that of caffeine and ryanodine. The fact that pharmacological blockers of CICR, such as procaine and ruthenium red, specifically inhibit the cADPR-sensitive release indicates that cADPR acts on the same $Ca^{+2}$ release system. This is further supported by the finding that low concentrations of cADPR that are not sufficient to induce $Ca^{+2}$ release can greatly potentiate the effect of caffeine. More direct demonstration of cADPR acting through the CICR system comes from the fact that cADPR can also potentiate the $Ca^{+2}$ release induced by divalent cations such as $Ca^{+2}$ and $Sr^{+2}$. Taken together these results show that cADPR is likely to be an endogenous regulator of the caffeine-sensitive CICR system in sea urchin eggs.

In this study we synthesized a series of analogs of cADPR. By altering the structure of cADPR and assessing resulting changes in its biological activity we hope to gain further insights into the mechanism of cADPR action. Results show that alterations at the 8-position of the adenine group did not inhibit cADPR from binding to its receptor but did eliminate its ability to activate $Ca^{+2}$ release. Furthermore, 8-amino-cADPR, the most potent antagonist synthesized, was also able to block the potentiating effect of cADPR on $Ca^{+2}$ release induced by divalent cations and caffeine.

EXPERIMENTAL PROCEDURES

Synthesis of 8-substituted Analogs of Cyclic ADP-ribose.

Figure 10:
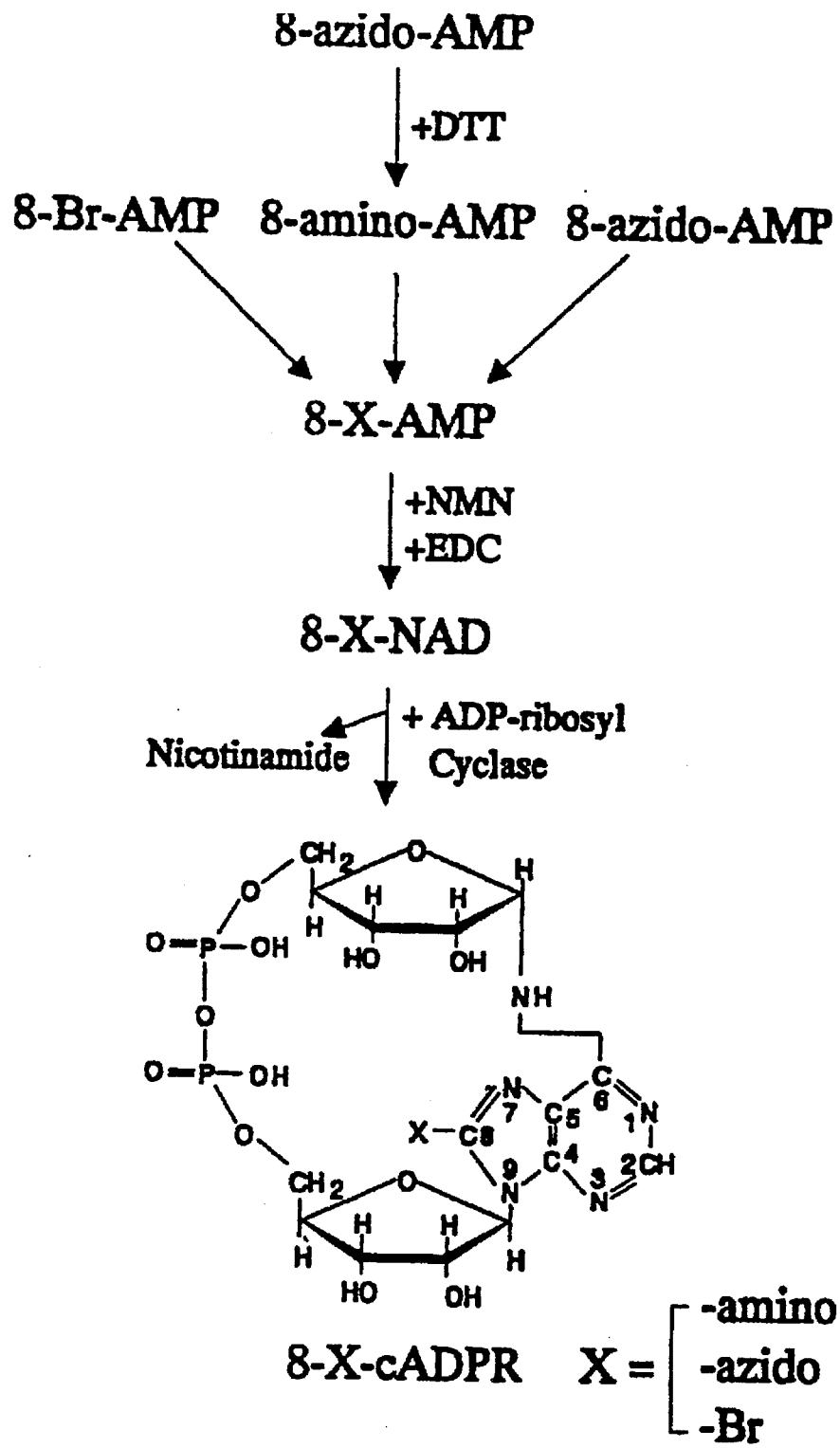
FIG. 10 Shows a scheme for making 8-X-cADPR.
Figure 11:
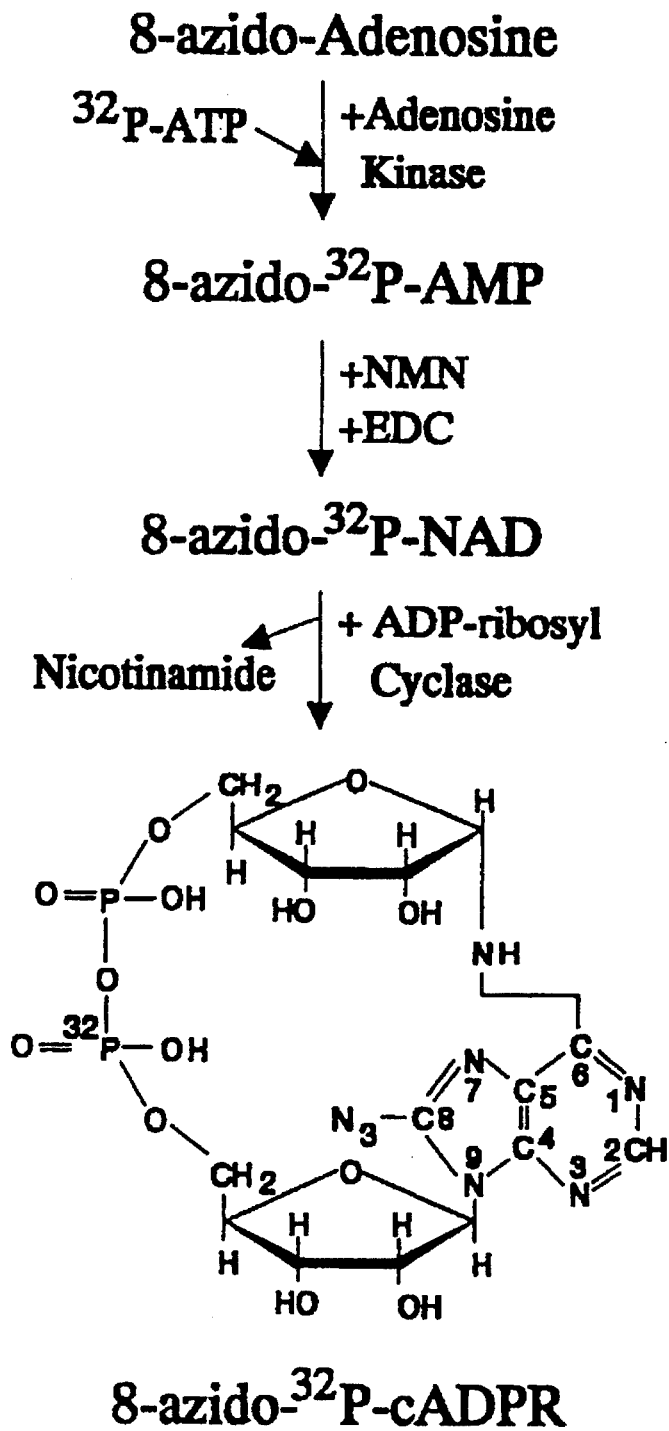
FIG. 11 shows a scheme for making 8-azido-$^{32}$P-cADPR.

8-substituted derivatives of cADPR were synthesized from commercially available precursors using a two step procedure consisting of the synthesis of 8-substituted $NAD^+$'s by chemically coupling 8-substituted AMP's to β-nicotinamide mononucleotide (β-NMN) followed by enzymatic conversion to 8-substituted cADPR. 8-amino-AMP was prepared by treatment of 8-azido-AMP with dithiothreitol as described by Cartwright et al. (Cartwright, I. L., Hutchinson, D. W., and Armstrong, V. W. (1976) *Nucleic Acids Research* 3, 2331–2339). 8 azido-AMP (9.8 μmol) was incubated in the dark for 4 to 16 hours in the presence of 50 mM triethylammonium bicarbonate, pH 8.8 and 15 mM dithiothreitol in a volume of 1 ml. The conversion of 8-azido-AMP to 8-amino-AMP was virtually complete and was followed by a shift in the absorption maxima from 281 nm to 274 nm. The resulting 8-amino-AMP was purified on a MONO Q HR (10/10) column eluted with a gradient of triethylammonium bicarbonate, pH 8.8 from 10 to 1000 mM over 30 minutes at a flow rate of 2 ml/min. The 8-amino-AMP peak, eluted at about 16 minutes, was collected and evaporated to dryness on a SpeedVac concentrator. FIG. 10 shows a general scheme for making 8-X-cADPR of the invention. FIG. 11 shows a scheme for making 8-azido-$^{32}$P-cADPR which is useful in photoaffinity labelling studies to track proteins.

The chemical coupling of 8-substituted AMP's to β-NMN to form 8-substituted $NAD^+$'s was performed by carbodiimide coupling essentially as described by Prescott and McLennan (Prescott, M. and McLennan, A. G. (1990) *Anal. Biochem.* 184, 330–337). 8-amino-AMP (0.1 μmol), β-NMN (1μmol) and $MgCl_2$ (2 μmol) were combined in a microfuge tube and evaporated to dryness using a SpeedVac concentrator. The coupling reaction was initiated by adding 20 μl of 1.5M HEPES-NaOH, pH 6.8 and 20 μl of 1.5M 1-ethyl-3(3-dimethyl-amino-propyl)-carbodiimide-HCl (EDC) and incubated at 37° C. for 12 to 18 hours. The yield of 8-amino-$NAD^+$ was between 40 and 50%. The reaction products were diluted to 1 ml with water and injected onto an AG MP 1 column (0.6×15 cm) which was eluted at a flow rate of 1 ml/min using a trifluoroacetic acid gradient from 1.5 to 150 mM over 30 minutes. The AG MP-1 purification system has been previously described (Lee, H. C. and Aarhus, R. (1991) *Cell Regulation* 2, 203–209, Axelson, J. T., Bodley, J. W., and Walseth, T. F. (1981) *Anal. Biochem.* 18, 333–364). The 8-amino-$NAD^+$ peak was collected and evaporated to dryness on a SpeedVac concentrator. The coupling reactions using 8-Br-AMP and 8-azido-AMP were done identically, except that all manipulations with 8-azido-compounds were done in the dark or reduced light. 8-amino-$NAD^+$ was converted to 8-amino cADPR using ADP-ribosyl cyclase purified from Aplysia ovotestis as previously described (Lee, H. C. and Aarhus, R. (1991) *Cell Regulation* 2, 203–209). The 8-amino-$NAD^+$ was reconstituted with 1 ml of 25 mM HEPES-NaOH, pH 6.8 and incubated for 2 to 4 hours at room temperature with 45.4 units of ADP-ribosyl cyclase (1 unit is defined as the amount of enzyme that produces 1 nmol of cADPR from 1 mM $NAD^+$ at room temperature and pH 6.8). The resulting 8-amino-cADPR was purified by AG MP-1 chromatography as described above. The purified 8-amino-cADPR was evaporated to dryness on a SpeedVac concentrator and stored at −20° C. The conversion of the 8-Br and 8-azido derivatives was identical to that described for 8-amino-NAD$^+$. The ADP-ribosyl cyclase recognized each of the 8-substituted NAD$^+$ derivatives and converted virtually all of the NAD$^+$ derivatives to the corresponding cADPR derivatives.

The molar extinction coefficients of 8-amino-, 8-Br—, and 8-azido-cADPR were determined by total phosphate analysis (Hess, H. H. and Derr, J. E. (1975) *Anal. Biochem.* 63, 607–613) using 5'-AMP as a standard. The $\lambda$max and $\epsilon_M$ at the $\lambda$max were: 274 nm, 16,000 M$^{-1}$ cm$^{-1}$ for 8-amino-cADPR; 264 nm, 15,730 M$^{-1}$ cm$^{-1}$ for 8-Br-cADPR; and 281 nm, 18,215 M$^{-1}$cm$^{-1}$ for 8-azido-cADPR.

Proton NMR spectrum of 8-amino-cADPR was obtained using a 500 MHz spectrometer (GE) as previously described (Lee, H. C., Walseth, T. F., Bratt, G. T., Hayes, R. N., and Clapper, D. L. (1989) *J. Biol. Chem.* 264, 1608–1615). The purified sample eluted from an AG MP-1 column was neutralized with KOH, lyophilized and reconstituted with D$_2$O. The mass of the negative molecular ion of 8-amino-cADPR was determined by fast atom bombardment mass spectrometry using triethanolamine as matrix.

Preparation of Sea Urchin Homogenates

Homogenates from *Strongylocentrotus purpuratus* eggs were prepared as previously described (Lee, H. C. (1991) *J. Biol. Chem.* 266, 2276–2281, Lee, H. C. (1993) *J. Biol. Chem.* 268, 293–299). Briefly, eggs were washed once in artificial sea water, twice in Ca$^{+2}$-free sea water containing 1 mM EGTA, twice in Ca$^{+2}$-free sea water without EGTA, once with the homogenization buffer (GluIAG MPM) containing 250 mM N-methylglucamine, 250 mM potassium gluconate, 20 mM HEPES, and 1 mM MgCl$_2$; pH titrated to 7.2 with acetic acid and resuspended with the same medium to 25% (v/v). The following additions were made: 10 µg/ml of leupeptin, 10 µg/ml of aprotinin, 50 µg/ml of soybean trypsin inhibitor, 2 units/ml of creatine kinase, 4 mM phosphocreatine and 0.5 mM ATP. The suspension was chilled on ice for 10–15 min and transferred to a beaker inside a cell disruption bomb (Parr Instrument Co., Ill.). The suspension was mixed continuously with a magnetic stirring bar while nitrogen pressure of 80 psi was applied for 10–30 seconds. The sudden decompression of the suspension as it was released from the bomb effectively homogenized the eggs. The homogenates were centrifuged for 12–14 seconds (13,000×g, 4° C.) in a microfuge (Fisher) and the supernatant was collected and stored frozen at −70 ° C. until use.

Homogenates (15% v/v) from *Lytechinus pictus* eggs were prepared as described above except that the homogenization was done using a Dounce-type homogenizer fitted with a size A pestle.

Measurements of Calcium Release from the Egg Homogenates.

Frozen egg homogenates prepared as described above were thawed in a 17° C. water bath for 20–30 min and then diluted to 5% with the homogenization medium (GLuIM) containing 2 units/ml of creatine kinase, 4 mM phosphocreatine and 0.5 mM ATP. After incubating at 17° C. for one hour the homogenates were diluted sequentially to 2.5% and finally to 1.25% with the same medium. Following each dilution, the homogenates were incubated at 17° C. for one hour. After the last dilution, fluo 3 was added to a final concentration of 3 µM. Fluorescence was measured at 490 nm excitation and 535 nm emission using a Hitachi spectrofluorimeter (F-2000). Fluo 3 fluorescence intensity is directly related to the Ca$^{+2}$ concentration (Dargie, P. J., Agre, M. C., and Lee, Hon. C. (1990) *Cell Regulation* 1,279–290). In some Figures the Fluo 3 fluorescence intensity was calibrated with the addition of known amounts of Ca$^{+2}$. All assays were done in a curvette maintained at 17° C. with a circulating water bath and its content continuously mixed with a magnetic stirring bar. The volume of homogenate used for each assay was 0.2 ml.

Measurements of Specific Cyclic ADP-ribose Binding.

Specific binding of [$^{32}$P]cADPR to sea urchin egg microsomes was determined by a filtration assay as described previously (Lee, H. C. (1991) *J. Biol. Chem.* 266, 2276–2281) with some modifications. *L. pictus* egg homogenates (1 ml) were dialyzed overnight against 1 liter of the homogenization buffer (GluIM listed above). After dialysis, the homogenates were centrifuged for 30 min in a microfuge and the supernatant containing microsomes was collected and diluted 20 fold with GluIM. About 40,000 cpm of [$^{32}$P]cADPR (400 Ci/mmol) and various concentrations of either cADPR or 8-substituted analogs were incubated with the 20 fold diluted microsomes for 10 min at 4° C. in a volume of 0.1 ml. Polyethylene glycol (MW 8,000) was added to a final concentration of 10% and after 3 min on ice the mixture was rapidly filtered through a pre-washed GF/F filter (Whatman) under vacuum. The filters were then washed with 4 ml of 10% polyethylene glycol and the radioactivity on the filters was determined by liquid scintillation counting. The GF/F filters were pre-washed twice with 4 ml of 10% polyethylene glycol. The specific binding was determined as the total binding minus the binding in the presence of 1.2 µM of unlabeled cADPR. *L. pictus* homogenates were used in the binding study because they have much higher binding capacity than those from *S. purpuratus*.

Synthesis of cADPR and Radioactive Labeled cADPR.

ADP-ribosyl cyclase was partially purified from Aplysia ovotestis as described previously (Lee, H. C. and Aarhus, R. (1991) *Cell Regulation* 2, 203–209). cADPR was synthesized by incubating 2–3 mM NAD$^+$ (pH 8.0) with the cyclase at room temperature and purified subsequently on an AG MP-1 column (Bio-Rad) using a gradient of trifluoroacetic acid as described above. Concentrations of the cADPR stock solutions were determined by absorbance at 254 nm and an extinction coefficient of 14,300 (Lee, H. C., Walseth, T. F., Bratt, G. T., Hayes, R. N., and Clapper, D. L. (1989) *J. Biol. Chem.* 264, 1608–1615).

[$^{32}$P]cADPR was synthesized using [$^{32}$P]NAD$^+$ (800 Ci/mmol) as substrate. After incubation with the Aplysia ADP-ribosyl cyclase, the product was purified using an AG MP-1 column as described for the preparation of unlabeled cADPR (Lee, H. C. and Aarhus, R. (1991) *Cell Regulation* 2, 203–209).

Materials

8-Br-AMP, 8-azido-AMP and nicotinamide mononucleotide were obtained from Sigma. Fluo 3 was from Molecular Probes. [$^{32}$P]NAD$^+$ was from New England Nuclear. Ryanodine was from CalBiochem. EDC was from Sigma.

RESULTS

FIG. 1 compares proton NMR spectra of 8-amino-cADPR with cADPR itself. The triplet between 5.2 ppm and 5.3 ppm is characteristic of cADPR and represents the 2' proton of the ribose unit that is linked to the adenine ring. As can be seen in FIG. 1, this triplet was present and unchanged in 8-amino-cADPR indicating that it was a cyclized product similar to cADPR. The peaks corresponding to the two anomeric protons (H1' and $H_A1'$ and the 2-proton on the adenine (HA2) were also present in the 8-amino cADPR spectrum but their chemical shifts were slightly altered as compared with those of cADPR, suggesting the conformation of 8-amino-cADPR may be different from that of cADPR. The peak corresponding to the 8-proton on the adenine ring was missing in the spectrum of 8-amino-cADPR, confirming its replacement by the amino group.

A mass of 555 was measured for the negative molecular ion ([M—H]) of 8-amino cADPR using fast atom bombardment mass spectrometry. It was, therefore, larger than cADPR by 15 units and is consistent with the replacement of the 8-proton by an amino group. The UV-spectrum of 8-amino-cADPR has a maximum at 274 nm which was different from the 260 nm maximum of cADPR (1). The extinction coefficient of 8-amino cADPR at 274 nm was determined to be 16,000 by total phosphate analysis. This value was used to determine the concentrations of 8-amino-cADPR used in the rest of the study.

Figure 2:
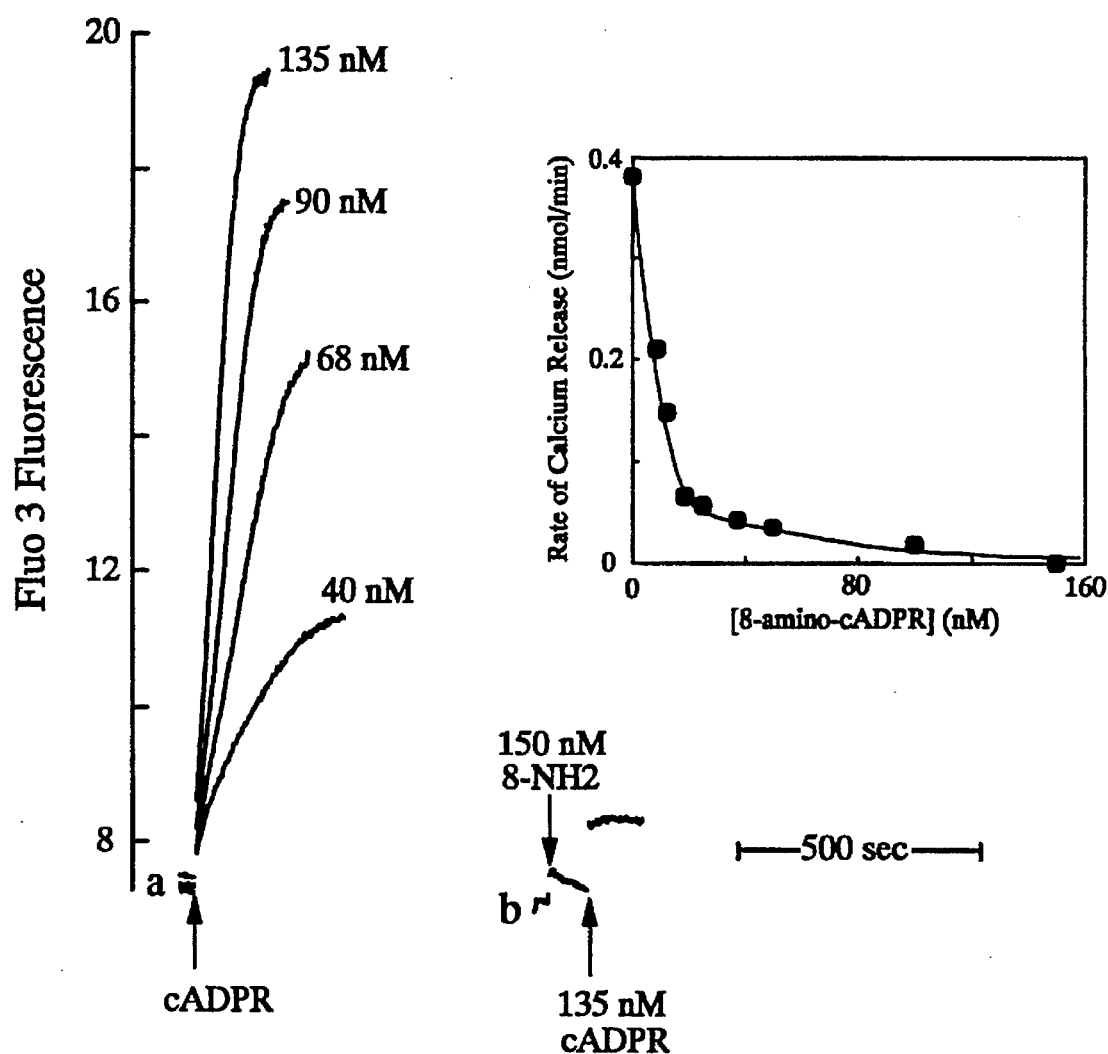
FIG. 2 Inhibition of cADPR induced $Ca^{+2}$ release by 8-amino-cADPR $Ca^{+2}$ release from *S. purpuratus* homogenates (1.25%) was monitored using Fluo 3 as $Ca^{+2}$ indicator. 8-amino-cADPR (8-$NH_2$) and cADPR were added to the homogenates to final concentrations indicated in the Figure. (a) The effect of varying the concentration of cADPR on $Ca^{+2}$ release. (b) The inhibition of $Ca^{+2}$ release induced by 135 nM of cADPR by pre-treatment of the homogenates with 100 nM 8-amino-cADPR. The inset shows the dependence of the inhibition on the concentration of 8-amino-cADPR.

The effects of 8-amino-cADPR on the $Ca^{+2}$ release induced by cADPR is shown in FIG. 2. Addition of 8-amino-cADPR to a final concentration of 150 nM to sea urchin egg homogenates did not cause any $Ca^{+2}$ release by itself but inhibited cADPR (135 nM) added subsequently from releasing $Ca^{+2}$ (trace b of FIG. 2). The small change in fluorescence immediately after the addition of 8-amino-cADPR shown in the Figure was due to slight contamination by $Ca^{+2}$ in the sample and not $Ca^{30\ 2}$ release from the microsomes. Comparison with the concentration-response curves shown in trace a of the FIG. 2, it can be seen that the block of $Ca^{+2}$ release by 8-amino-cADPR was virtually complete. The inset in the FIG. 2 shows the concentration dependence of the inhibition on cADPR-sensitive $Ca^{+2}$ release by 8-amino-cADPR. In the presence of about 9 nM 8 amino-cADPR, the rate of $Ca^{+2}$ release induced by 135 nM of cADPR was reduced by half.

Figure 3:
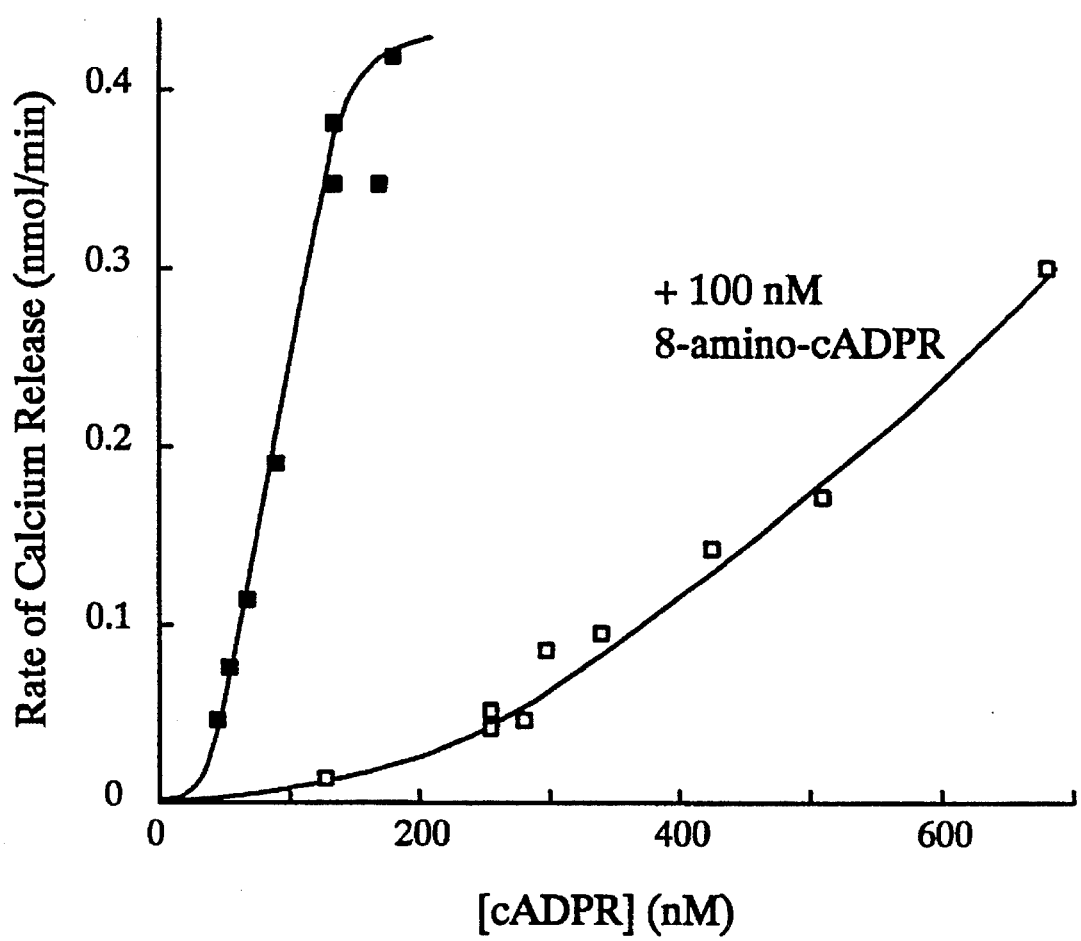
FIG. 3 Competitive inhibition of cADPR dependent $Ca^{+2}$ release by 8-amino-cADPR. $Ca^{+2}$ release from *S. purpuratus* homogenates (1.25%) induced by various concentrations of cADPR was measured in the presence and absence of 100 nM 8-amino-cADPR (8-amino-cADPR)

FIG. 3 compares the concentration-response curves of cADPR in the presence and absence of 8-amino-cADPR. In the absence of the analog, the half-maximal concentration of cADPR for $Ca^{+2}$ release was about 90 nM. The presence of 100 nM 8-amino-cADPR shifted the concentration-response curve toward higher concentrations of cADPR. These results show that the inhibitory effect of 8-amino-cADPR could be overcome by increasing the concentration of cADPR. The analog was therefore a reversible antagonist of cADPR.

Figure 4:
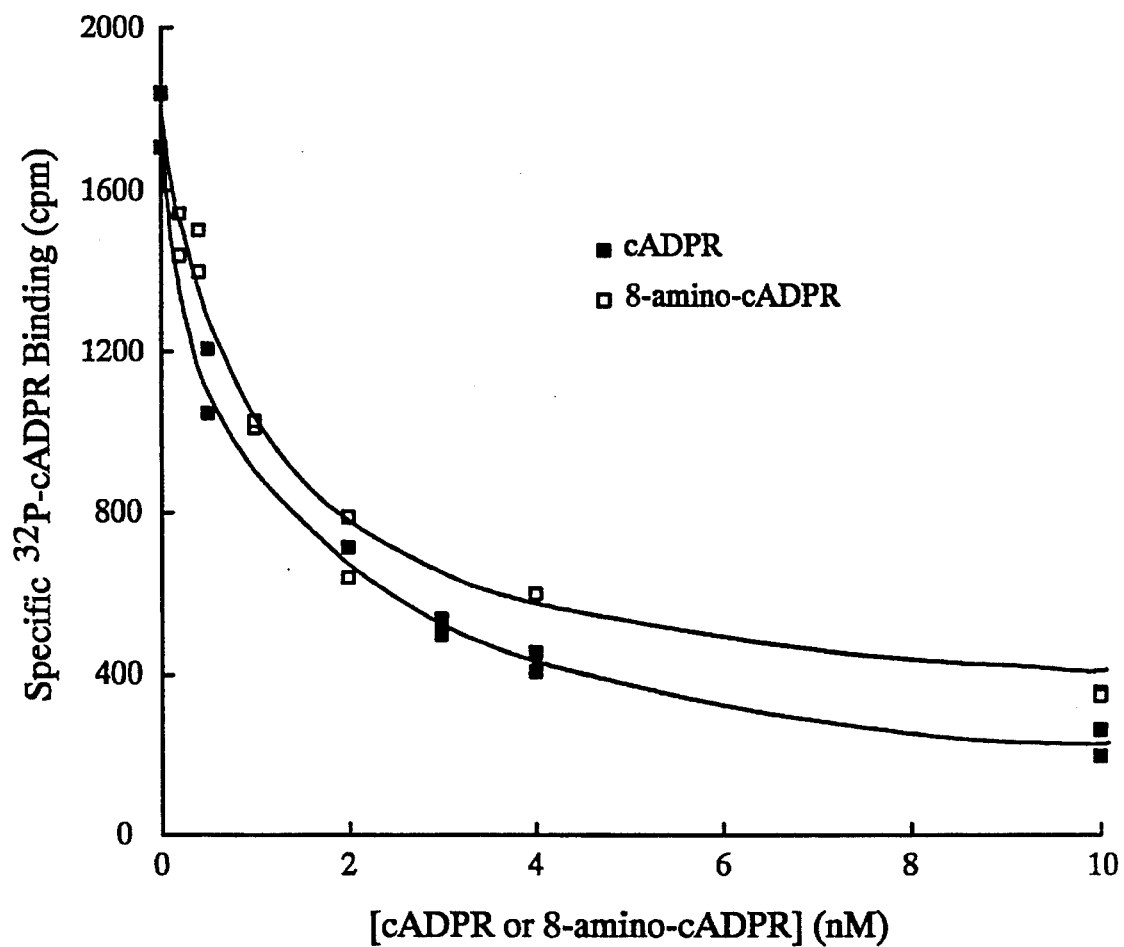
FIG. 4 Competitive inhibition of $^{32}$P-cADPR binding by 8-amino-cADPR and cADPR. Specific binding of $^{32}$P-cADPR to *L. pictus* microsomes was measured in the presence of various concentrations of cADPR (filled squares) and 8-amino-cADPR (open squares). Total binding in the presence of a high concentration of cADPR (1.2 µM) was taken as non-specific binding (55 cpm) and was subtracted from all the values.

FIG. 4 shows that 8-amino-cADPR was an effective competitor for the cADPR binding site. Specific binding of [$^{32}$]cADPR to sea urchin egg microsomes was measured in the presence of various concentrations of unlabeled cADPR or 8-amino-cADPR. As can be seen from the data, 8-amino-cADPR was as effective as cADPR itself in competing for the binding sites. Indeed, the two appeared to be indistinguishable.

The apparent affinity constant of cADPR derived from the binding data (~1 nM) was quite different from that derived from the $Ca^{+2}$ release measurements shown in FIG. 3. The reason for the discrepancy is not known but could be due to several possibilities. The most obvious one is that the conditions used for the two types of measurements were quite different. The $Ca^{+2}$ release was measured using $S.$ $purpuratus$ homogenates at 17° C. in the presence of ATP, whereas the binding was determined using dialyzed $L.$ $pictus$ homogenates at 0°–5° C. in the absence of ATP. On the other hand, the discrepancy could be real and would suggest that the binding site for cADPR and the $Ca^{+2}$ release mechanism may be separate entities as will be discussed in more details later.

Figure 5:
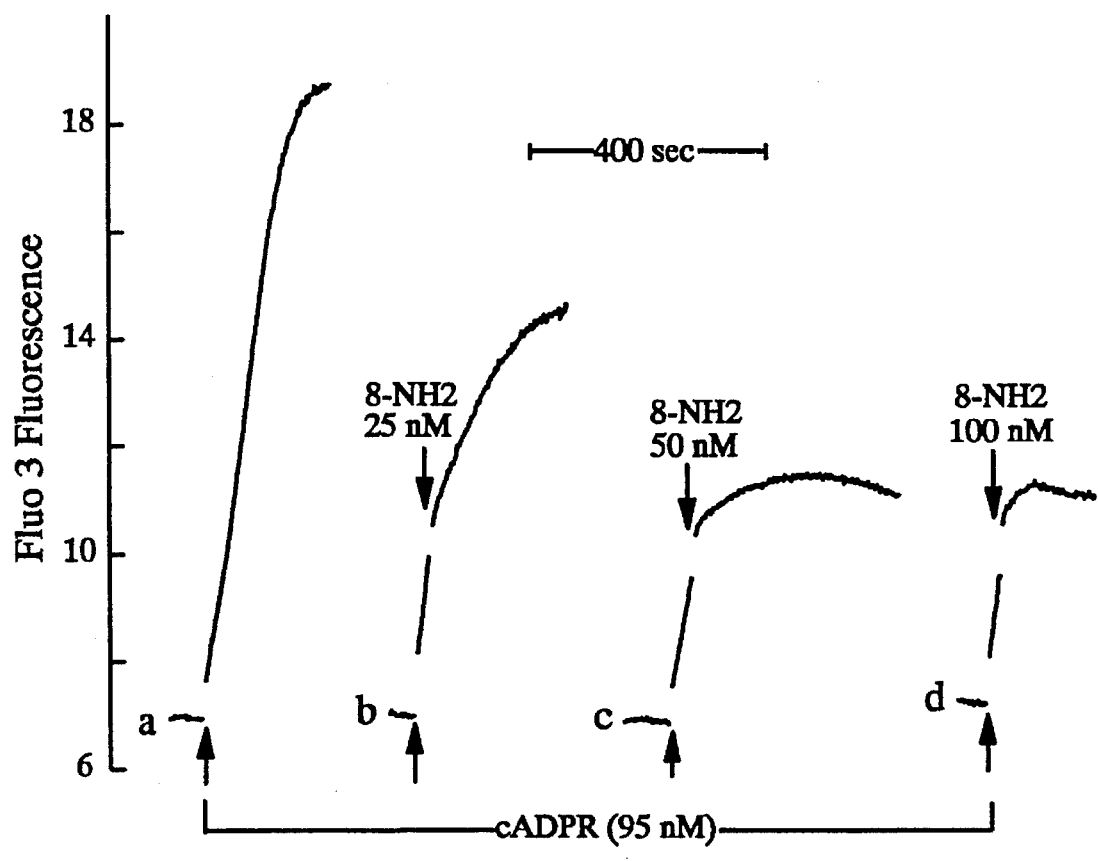
FIG. 5 Effectiveness of 8-amino-cADPR in blocking $Ca^{+2}$ release induced by cADPR. (a) $Ca^{+2}$ release from *S. purpuratus* homogenates (1.25%) induced by the addition of 95 nM cADPR was measured using Fluo 3 as $Ca^{+2}$ indicator. (b-d) After the $Ca^{+2}$ release had started, increasing amounts of 8-amino-cADPR (8-$NH_2$) were added to give the final concentrations indicated in the Figure.

The above results show that 8-amino-cADPR binds readily to the cADPR-binding site. However, because of the amino group at the 8-position, the bound analog can not activate the $Ca^{+2}$ release mechanism. Prior occupation of the cADPR binding sites by the analog would, therefore, reversibly inhibit cADPR from activating $Ca^{+2}$ release. That 8amino-cADPR can actually displace cADPR from its binding site is shown in FIG. 5. $Ca^{+2}$ release was activated by the addition of 95 nM cADPR (Trace a) and shortly after the release had commenced, increasing concentrations of 8-amino-cADPR were then added (trace b-d). This resulted in immediate reduction in the rate of $Ca^{+2}$ release and almost total cessation at the highest concentration (100 nM) of the antagonist used (trace d). It thus appears that $Ca^{+2}$ release requires continuous occupation of the binding site by cADPR and its displacement from the site by 8-amino-cADPR causes immediate closure of the release channel.

Figure 6:
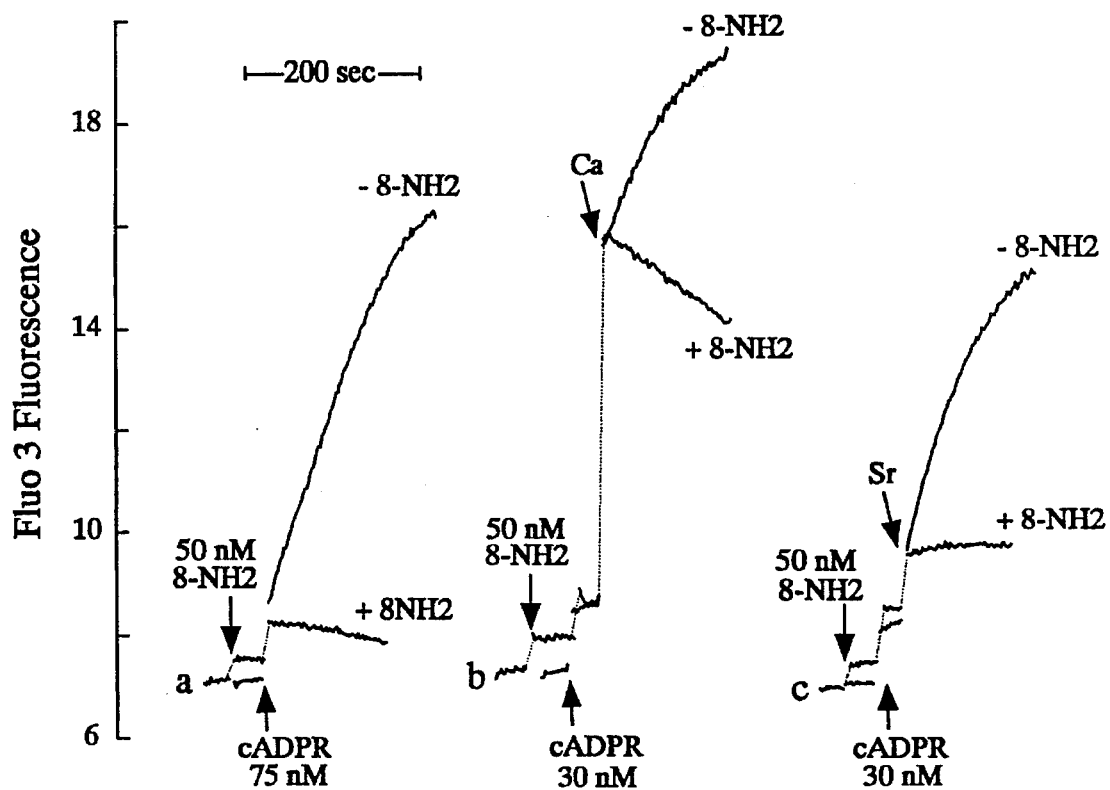
FIG. 6 Inhibition of the potentiating effect of cADPR on $Ca^{+2}$ release induced by divalent cations. $Ca^{30\ 2}$ release from *S. purpuratus* homogenates (1.25% ) was measured using Fluo 3 as $Ca^{+2}$ indicator. (a) $Ca^{+2}$ release was induced by 75 nM cADPR in the absence of 8-amino-cADPR (–8-$NH_2$). Prior addition of 50 nM 8-amino-cADPR (+8 $NH_2$) prohibited cADPR (75 nM) from releasing $Ca^{+2}$. (b) In the presence of 30 nM cADPR, addition of 0.4 nmol of $Ca^{+2}$ (arrow labeled Ca) induced further $Ca^{+2}$ release (–8-$NH_2$). Prior addition of 50 nM 8-amino-cADPR blocked cADPR from potentiating the $Ca^{+2}$ induced $Ca^{+2}$ release (+8-$NH_2$). (c) In the presence of 30 nM cADPR, addition of 2 nmol of $Sr^{+2}$ (arrow labeled Sr) induced further $Ca^{+2}$ release (–8-$NH_2$). Prior addition of 50 nM 8-amino-cADPR blocked cADPR from potentiating the $Sr^{+2}$ induced $Ca^{+2}$ release (+8-$NH_2$)

Accumulating evidence indicates that cADPR may act through a $Ca^{+2}$ release system similar to the $Ca^{+2}$ induced $Ca^{+2}$ release described in sacroplasmic reticulum (Galione, A., Lee, H. C. and Busa, W. B. (1991) *Science* 253, 1143–1146, Lee, H. C. (1993) *J. Biol. Chem.* 268, 293–299). In particular, it has been shown that low concentrations of cADPR that are not sufficient to release $Ca^{+2}$ can potentiate the $Ca^{+2}$ release induced by divalent cations and caffeine. Effects of 8-amino-cADPR on cADPR-potentiation of divalent cation induced $Ca^{+2}$ release are shown in FIG. 6. Trace a shows, as controls, the $Ca^{+2}$ release induced by 75 nM cADPR (−8-NH$_2$) and the total blockage of $Ca^{+2}$ release by prior addition of 50 nM 8-amino-cADPR (+8-NH$_2$). Trace b shows that, in the presence of 30 nM cADPR, addition of 0.4 nmol of $Ca^{+2}$ abruptly increased the $Ca^{+2}$ level of the homogenate, which was followed by a slower stimulated release of more $Ca^{+2}$ (curve labeled+8-NH$_2$). This stimulated release was absent when 50 nM 8-amino-cADPR was added prior to the addition of 30 nM cADPR (curve labeled+8-NH$_2$ of trace b). Instead, the $Ca^{+2}$ level declined following the initial abrupt increase, which was due to sequestration of the added $Ca^{+2}$ by the thapsigargin sensitive $Ca^{+2}$ transport system in the egg homogenates (Lee, H. C. (1993) *J. Biol. Chem.* 268, 293–299). These characteristics of $Ca^{+2}$ changes in the presence of 8-amino cADPR were virtually identical to the control when $Ca^{+2}$ was added to egg homogenates in the absence of both cADPR and the analog (data not shown, cf Lee, H. C. (1993) *J. Biol. Chem.* 268, 293–299).

Similarly, addition of another divalent cation $Sr^{+2}$ in the presence of 30 nM cADPR stimulated further $Ca^{+2}$ release as shown in Trace c of FIG. 6 (curve labeled—8-NH$_2$). Again, this stimulated release was blocked by prior addition of 50 nM 8-NH$_2$ (curve labeled+8-NH$_2$ of trace c). These results indicate that 8-amino-cADPR not only can inhibit the cADPR-sensitive $Ca^{+2}$ release it can also block cADPR from potentiating $Ca^{+2}$ release induced by divalent cations such as $Ca^{+2}$ and Sr+2. In FIG. 6c, the $Ca^{+2}$ sequestration after the addition of $Sr^{+2}$ appeared to be inhibited. It is likely due to $Sr^{+2}$ competing for the $Ca^{+2}$ pump site.

Figure 7:
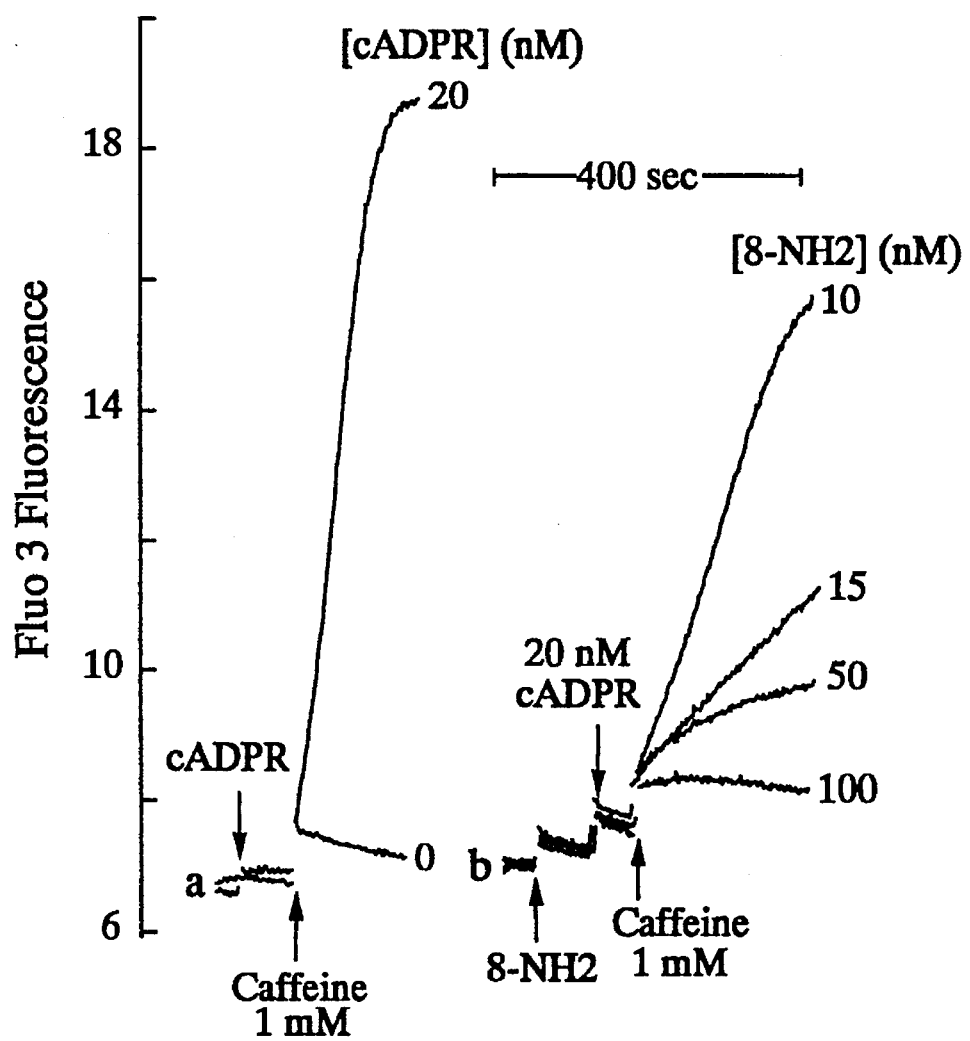
FIG. 7 Inhibition of the potentiating effect of cADPR on caffeine induced $Ca^{+2}$ release. $Ca^{+2}$ release from *S. purpuratus* homogenates (1.25%) was measured using Fluo 3 as $Ca^{+2}$ indicator. (a) In the absence of cADPR, addition of 1 mM caffeine induced no $Ca^{+2}$ release (curve labeled 0). The presence of 20 nM cADPR (arrow labeled cADPR) greatly potentiated the $Ca^{+2}$ releasing activity of 1 mM caffeine (curve labeled 20). (b) Prior addition of increasing concentrations of 8-amino-cADPR (8-$NH_2$, 10–100 nM) progressively inhibited cADPR (20 nM) from potentiating the $Ca^{+2}$ releasing activity of 1 mM caffeine.

Another commonly used index for $Ca^{+2}$-induced $Ca^{+2}$ release is sensitivity to caffeine. Consistent with previous results (Lee, H. C. (1993) *J. Biol. Chem.* 268, 293–299), trace a of FIG. 7 shows that in the absence of cADPR (curve labeled 0) addition of 1 mM caffeine did not produce any $Ca^{+2}$ release. However, a low concentration of cADPR (20 nm), which was not sufficient to release $Ca^{+2}$ by itself, greatly increased the caffeine sensitivity of the system such that a large release could now be produced by 1 mM caffeine (curve labeled 20). This potentiating effect of cADPR on the caffeine sensitivity was blocked by 8-amino-cADPR as shown in trace b. Comparison between trace a (curve labeled 20) with trace b (curve labeled 10) shows that prior addition of as low as 10 nM 8-amino-cADPR produced substantial inhibition in the potentiation of caffeine induced $Ca^{+2}$ released by cADPR (20 nm) and was completely blocked by 100 nM 8-amino-cADPR (curve labeled 100 in trace b).

Figure 8:
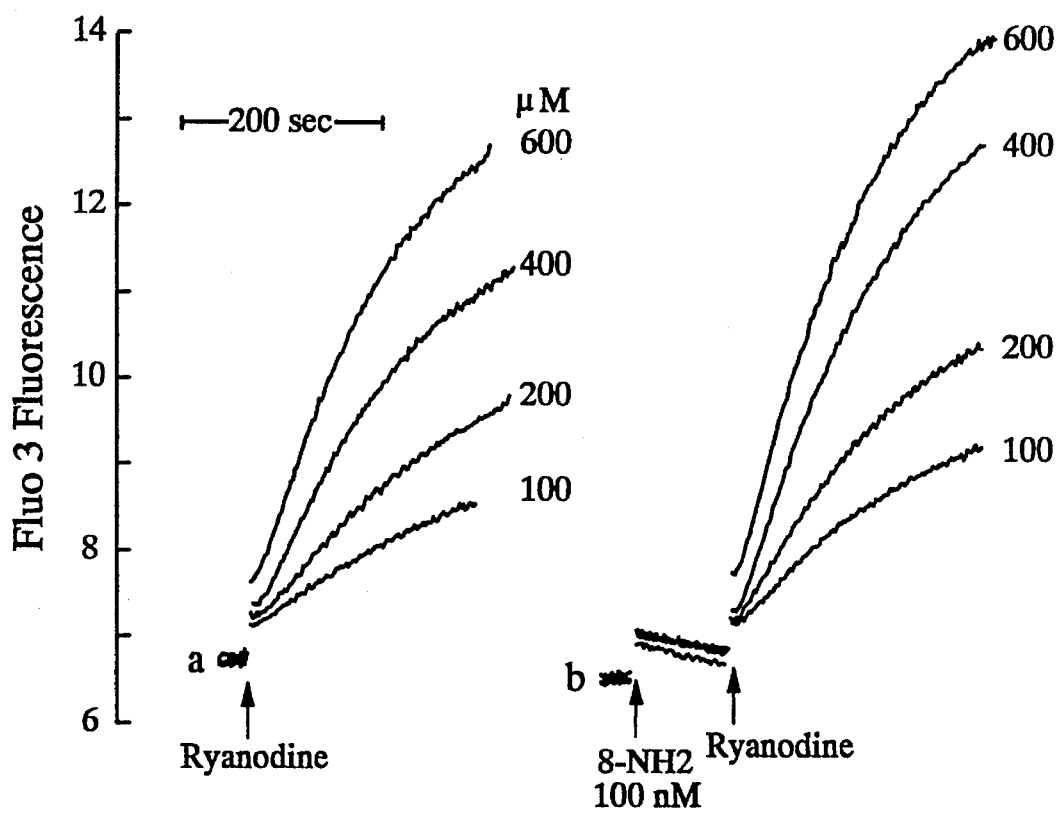
FIG. 8 Inability of 8-amino-cADPR to block $Ca^{+2}$ release induced by ryanodine. $Ca^{+2}$ release from *S. purpuratus* homogenates (1.25%) was measured using Fluo 3 as $Ca^{+2}$ indicator. Ryanodine and 8-amino-cADPR (8-$NH_2$) were added to the final concentrations as indicated.

It is generally accepted that the $Ca^{+2}$ releasing effect of caffeine is through its action on the ryanodine receptor (Endo, M. (1977) *Physiol. Rev.* 57, 71–108). FIG. 8 shows that addition of ryanodine to egg homogenates produced a concentration-dependent release of $Ca^{+2}$ (trace a). These results confirm previous observations on another species of sea urchin (Galione, A., Lee, H. C. and Busa, W. B. (1991) *Science* 253, 1143–1146) and indicate the presence in the eggs of a $Ca^{+2}$ release mechanism very similar to the ryanodine-receptor in muscle. Trace b shows that the presence of 100 nM of 8-amino-cADPR did not inhibit the $Ca^{+2}$ release induced by ryanodine. In fact, if any, the $Ca^{+2}$ release activity of ryanodine appears to be slightly stimulated by 8-amino-cADPR. Similarly, 100 nM of 8 amino-cADPR also did not block the $Ca^{+2}$ release-induced by a high concentration of caffeine (2.5 mM, data not shown). The inhibitory effect of 8-amino-cADPR, therefore, was specifically on the potentiation by cADPR and not on the $Ca^{+2}$ release mechanism activated by either caffeine or ryanodine itself. These results suggest that cADPR and caffeine (or ryanodine) either act on different sites on the same $Ca^{+2}$ release channel or actually on different molecules.

Figure 9:
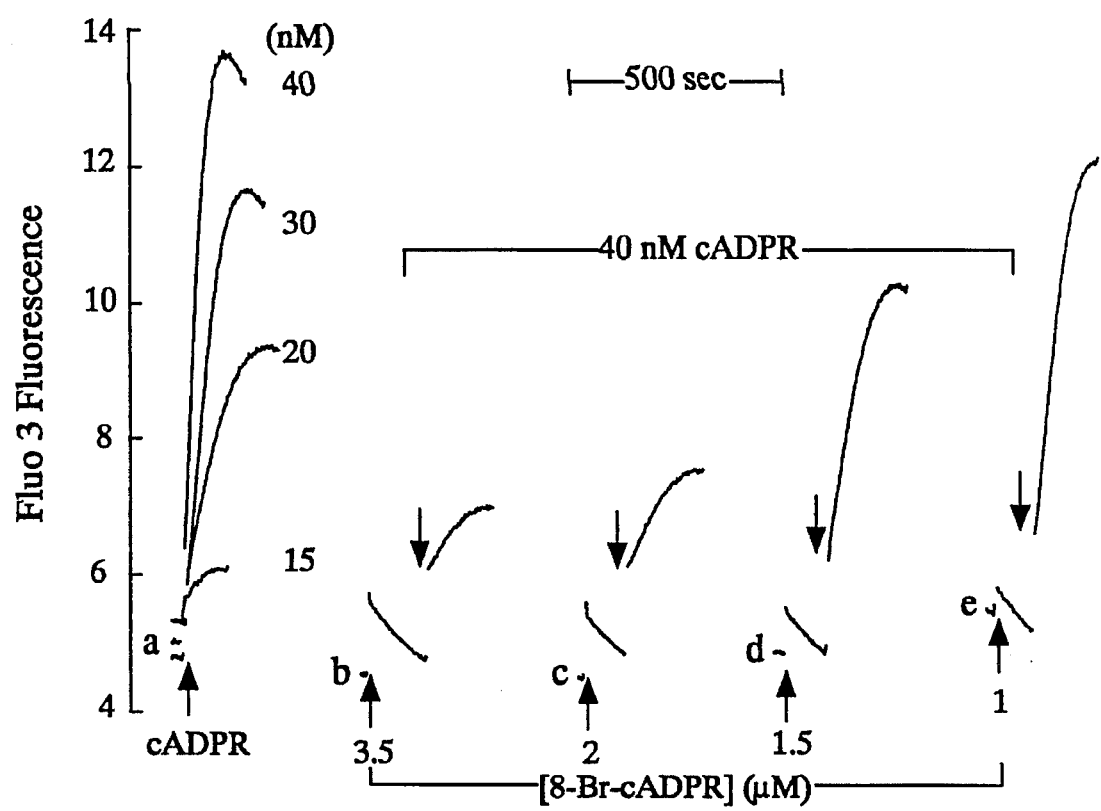
FIG. 9 Inhibition of cADPR induced $Ca^{+2}$ release by 8-Br-cADPR. (a) $Ca^{+2}$ release from *L. pictus* homogenates (2.5%) induced by increasing concentrations of cADPR (15–40 nM) was measured by using Fluo 3 as $Ca^{+2}$ indicator. (b-e) Prior addition of increasing concentrations of 8-Br-cADPR (1 µM in e to 3.5 µM in b) did not release any $Ca^{+2}$ but progressively inhibited cADPR (40 nM) from releasing $Ca^{+2}$.

In addition to 8-amino-cADPR, two other 8-substituted analogs of cADPR were also synthesized. FIG. 9 shows that prior addition of increasing concentrations of 8-Br cADPR (trace e-b) did not release $Ca^{+2}$ by themselves but produced progressive blockage of $Ca^{+2}$ release induced by 40 nM cADPR as compared with controls without the analog (trace a). 8-Br-cADPR was not as effective as 8-amino-cADPR and required micromolar concentrations. Similar antagonistic effect was also seen with 8-azido-cADPR and its potency was found to be between that of 8-amino-cADPR and 8-Br-cADPR (data not shown). These results indicate the 8-position of the adenine ring in cADPR is of crucial importance to the $Ca^{+2}$ release activity of the molecule and alterations at that position can convert an agonist (cADPR) to antagonists with various potencies.

DISCUSSION

In this study, a procedure was devised to produce 8-substituted analogs of cADPR. By altering the structure of cADPR and assessing the resulting change in its biological activity, we hope to gain insights into the mechanism of its action. None of the analogs synthesized in this study was able to induce $Ca^{+2}$ release indicating that the 8 position of the adenine ring is of crucial importance for activating the $Ca^{+2}$ release mechanism. Competitive binding studies show that the analogs, nevertheless, were able to interact with the binding site for cADPR. Occupation of the binding site is, therefore, necessary but not sufficient condition for activation of the release mechanism. A specific interaction between the binding site and the group at the 8-position of cADPR is also required. Since the analogs can bind to the binding site but cannot activate the release mechanism one would expect them to be antagonists. Indeed, the analogs were able to block cADPR from activating $Ca^{+2}$ release. Furthermore, the inhibition was reversible since it could be overcome by high concentrations of cADPR. The antagonistic effects of the analogs can thus be explained by competition between cADPR and the analogs for the occupation of the binding site.

Of the series of three compounds characterized in this study, the group at the 8 position of the adenine ring is the smallest in cADPR which is a hydrogen. In this case, the compound is an agonist which can both bind and effectively activate the $Ca^{+2}$ release mechanism. Changing the size of the group from a hydrogen to an amino-group, an increase of 15 atomic units, resulted in minimal change in binding affinity but the bound analog cannot activate the release mechanism. The analog, therefore, becomes the most effective antagonist of the series. Further increase in the size to azido- (42 atomic units) and bromo-group (79 atomic units) resulted in a substantial decrease in antagonist activity, which could very well be due to steric hindrance reducing the binding affinity of the analogs. It thus appears that the size of the group at the 8-position of the adenine ring is crucial to the biological activity.

Generally, when X of 8-X-cADPR is as large or larger than iodine in atomic weight, the compound is not a useful antagonist. Additionally, it has been found that X may not be a thiol group.

Accumulating evidence (Galione, A., Lee, H. C. and Busa, W. B. (1991) *Science* 253, 1143–1146; Galione, A. (1992) *Trends Pharmacol. Sci.* 13, 304–306; Lee, H. C. (1993) *J. Biol. Chem.* 268, 293–299) indicates that cADPR is operating through a $Ca^{+2}$ release mechanism very similar to the CICR system described in muscle (Endo, M. (1977) *Physiol. Rev.* 57, 71–108; Fleischer, S. and Inui, M. (1989) *Annu. Rev. Biophys. Chem.* 18, 333–364). It is generally accepted that CICR is mediated by the ryanodine receptor which has recently been sequenced (Takeshima, T., Nishimura, S., Matsumoto, T., Ishida, H., Minamino, N., Matsuo, H., Ueda, M., Hanaoka, M., Hirose, T., and Numa, S. (1989) *Nature* 339, 439–445). Indeed, a protein similar to the skeletal muscle ryanodine receptor has been identified in sea urchin eggs by specific antibody cross reactivity (Prescott, M. and McLennan, A. G. (1990) *Anal. Biochem.* 184, 330–337). Whether cADPR acts directly on this ryanodine-like protein remains to be established.

An alternative possibility has been proposed to account for the potentiation of the $Ca^{+2}$ release activity of caffeine by cADPR (Lee, H. C. (1993) *J. Biol. Chem.* 268, 293–299). This proposal suggests that the binding site for cADPR is a separate entity which after binding cADPR can then interact with the caffeine site of the ryanodine-like channel resulting in activation of $Ca^{+2}$ release. The receptor-cADPR complex, therefore, behaves like localized caffeine. Both caffeine and cADPR, therefore, act by sensitizing the ryanodine-like channel to divalent cations. The results presented in this study are consistent with this proposal. We have shown that 8 amino-cADPR, in addition to inhibiting cADPR from releasing $Ca^{+2}$, can also block cADPR from potentiating $Ca^{+2}$ release induced by divalent cations and caffeine. The antagonist, however, does not block $Ca^{+2}$ release induced by either caffeine itself or ryanodine. A straight forward interpretation of these result s is that caffeine (or ryanodine) and cADPR act on different sites. By displacing cADPR from its binding site, the antagonist could render the binding site incapable of interacting with the caffeine site on the ryanodine-like channel. As a result, both the potentiating effects on caffeine and divalent cations as well as the $Ca^{+2}$ releasing activity of cADPR are blocked. The channel, however, can still be activated by caffeine or ryanodine directly. If the binding site for cADPR and the $Ca^{+2}$ release channel were indeed two separate entities, the concentration-response curves of cADPR for $Ca^{+2}$ release and receptor binding would not necessarily be the same. In fact, as shown in FIG. 3 and 4, they were found to be quite different. Although part of the discrepancy could be due to the difference in conditions used in the measurements.

In this study, we demonstrate the feasibility of synthesizing analogs of cADPR. These analogs should provide useful tools for elucidating the mechanism and function of the cADPR system. For example, it is possible to introduce antagonists such as 8-amino cADPR into cells and determine which cellular function(s) is blocked by the antagonist. This would provide clues for the kind of cellular functions the cADPR system regulates. Also, 8-azido-cADPR could be used as a photoaffinity label for identifying the binding site, which would settle the question of whether cADPR acts directly on the ryanodine like channel.

Calcium channel blockers can be concentrated and incorporated into controlled release polymers as an alternative mode of administering the drug (e.g., transdermal administration). Examples of controlled release polymers have been described by Folkman and Langer, U.S. Pat. No. 4,391,727, issued Jul. 5, 1983; Yolles, U.S. Pat. Nos. 3,880,991, issued Apr. 29, 1975, and 3,887,699, issued Jun. 3, 1975; Boswell, U.S. Pat. No. 3,773,919, the teachings of which are incorporated herein by reference. Preferably, biodegradable polymers will be used.

Uses cADPR is useful for causing release of calcium ions from internal stores in cells. Such release of calcium ions can cause cellular death. $Ca^{+2}$ is of enormous importance in biological systems playing crucial roles in many cellular functions including early events after fertilization, muscle contraction, secretion of neurotransmitters, hormones and other compounds, and as a second messenger activating various enzymes. cADPR is as potent as $IP_3$ in releasing $Ca^{+2}$ from intracellular stores. Thus, cADPR can replace $IP_3$ use in therapy and research.

Analogs of cADPR can block the effect of cADPR on cADPR-receptors. These blocking analogs are useful to block the normal influence of naturally occurring cADPR. Such analogs are thus useful pharmaceutical agents for diseases, such as hypertension.

For research purposes, 8-X-cADPR of the invention may be used for elucidating the mechanism and function of the cADPR system. Introduction of the antagonists of the invention into cells can be used to determine which cellular function(s) is blocked by the antagonist. This would provide the research with more insight as to the kind of cellular functions the cADPR system regulates.

8-azido-cADPR could be used as a photoaffinity label for identifying the binding site. See FIG. 11 for a scheme to make [$^{32}$P]8-azido-cADPR. Other radiolabels such as $^{14}$C and $^3$H may be used to track the 8-X-cADPR in a cellular system. Basically, the radioactive material is incorporated into the backbone or intermediates which are available with radiolabels from chemical supply houses.

[$^{32}$P]8-azido-cADPR may be used by incubating it with the cell sample and irradiating the sample with UV light. After photolysis, autoradiography, and densiometric analyses may be made.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

This completes the description of the preferred and alternate embodiments of the invention. Those skilled in the art may recognize other equivalents to the specific embodiment described herein which equivalents are intended to be encompassed by the claims attached hereto.

What is claimed is:

1. A compound of the formula:

8-X-cADPR wherein
X is selected from the group consisting of amino, azido, Br or a pharmaceutically acceptable acid addition salt thereof.

2. The compound of claim 1 wherein at least one phosphorus is $^{32}$P or $^{33}$P.

3. The compound of claim 1 wherein at least one carbon is $^{14}$C.

4. The compound of claim 1 wherein at least one non-exchangeable hydrogen is $^3$H.

* * * * *